United States Patent [19]

Scheifinger

[11] 4,336,250
[45] Jun. 22, 1982

[54] LACTATION IMPROVEMENT METHOD

[75] Inventor: Curtis C. Scheifinger, Morristown, Ind.

[73] Assignee: Eli Lilly and Company, Indianapolis, Ind.

[21] Appl. No.: 255,901

[22] Filed: Apr. 20, 1981

[51] Int. Cl.³ .................... A61K 37/00; A61K 31/70
[52] U.S. Cl. .................................. 424/177; 424/180; 424/115
[58] Field of Search ............... 424/177, 272, 180, 115

[56] References Cited

U.S. PATENT DOCUMENTS 4,218,560  8/1980  Maehr ................................ 424/180

OTHER PUBLICATIONS

Dzingaite–Chem. Abst., vol. 64 (1966), p. 11729h.
Dzingaite–Chem. Abst., vol. 58 (1963), p. 1756d.
Pankhurst and McGowan, Ellinbank Dairy Research Institute Report, Austrailia, 1978.

*Primary Examiner*—Sam Rosen
*Attorney, Agent, or Firm*—Charles W. Ashbrook; Arthur R. Whale

[57] ABSTRACT

Milk production in lactating ruminants is improved by the oral administration of an antibiotic selected from the virginiamycin or elfamycin families of antibiotics.

8 Claims, No Drawings

LACTATION IMPROVEMENT METHOD

BACKGROUND OF THE INVENTION

Both the virginiamycin and elfamycin families of antibiotics represent rather small and homogeneous groups of chemical agents which display interesting biological activity. The compounds are produced by fermentation of microorganisms of the streptomyces or actinoplanes species. All of the antibiotics of the virginiamycin family can be assigned to either one of the two basic primary structures known as A and B. An extensive review of the structure and mechanisms of action of the virginiamycin antibiotics is presented by Cocito in *Microbiological Reviews*, 43, pp 145-198 (1979). Certain of the elfamycins are discussed by Maehr et al., in *Journal of Antibiotics*, 361 (1979).

While the virginiamycins and elfamycins have been employed primarily in the treatment of bacterial infections, they also have found utility in the promotion of growth in domestic animals. As pointed out by Lucas in *Proc. Nutr. Soc.* (1972), 31, pp 1-8, virginiamycins are employed as growth stimulants for both poultry and swine. Virginiamycins also have been used in the form of feed additives to effect growth promotion in ruminants such as sheep and cattle. Maehr, in U.S. Pat. No. 4,218,560, describes the use of certain elfamycins as growth promotants in farm animals, including cattle.

Cocito reports that the virginiamycin compounds are effective in promoting growth in animals by the inhibition of the intestinal flora, particularly of gram-positive bacteria which interfere with the absorption of nutrients. While the precise mode of action is not known, it is established that this class of antibiotics is effective in promoting nutrient absorption and growth rate of several farm animals. Their commercial use as growth promoters is particularly favorable since they display extremely low toxicity, there is a lack of accumulation in animal tissues, there is practically an undetectable production of resistant mutants in the intestinal flora, and they are biodegradable in animal feces.

While the virginiamycins and elfamycins have been employed in the growth stimulation of ruminants which are grown for meat production for human consumption, the antibiotics heretofore have not been employed in lactating ruminants. It has now been found that when administered to lactating ruminants, the compounds do not promote growth of the animal, but instead cause an improvement in the milk which is produced. A typical improvement effected in increased production without an adverse affect on milk fat or protein content.

This nutritive response is particularly surprising in view of the mechanism of feed utilization by ruminant animals. Carbohydrates, which are the primary nutritive portion of ruminant feed, is degraded in the rumen to pyruvate, which in turn is metabolized to acetate, propionate and butyrate. The latter are collectively known as volatile fatty acids (VFA's).

The VFAs are absorbed from the gut and employed for energy production and growth. It is known that propionate is much more efficiently utilized than either acetate or butyrate. Some of the agents which are known to increase feed utilization efficiency accordingly operate by altering the ruminant fermentation process so that propionate production is increased at the expense of acetate and butyrate. Agents which cause an increase in propionate with a concomitant decrease in acetate cause ruminants growth for meat production to gain more weight without consuming more feed, or to maintain a normal weight pattern while consuming less feed. Such agents are therefore very beneficial to the beef industry.

The requirements and objectives of feed utilization of lactating ruminants such as dairy cows differ considerably from those of ruminants raised for meat production. Ruminal VFA production is of course of primary importance, since it relates directly to the normal maintenance of the animal, as well as to the quality and quantity of the milk produced by the animal. In the lactating ruminant, however, energy for lactation is the most limiting factor in milk production. Acetate is required for milk fat synthesis, while propionate is utilized to produce glucose, which in turn is required for lactose synthesis, and also has a minor role in milk fat production. Butyrate is more glycogenic than lipogenic, the lipogenic aspect being indirect since butyrate must first be degraded to acetate units before it can be utilized for long chain fatty acid synthesis, i.e., milk fat.

Accordingly, in order to increase milk production in lactating ruminants, it is necessary to alter ruminant fermentation (ie. VFA production), but not at a dramatic expense of either acetate or butyrate production. Significantly reduced acetate and butyrate levels result in drastically reduced milk fat content, thereby rendering milk production less efficient with respect to both quality and economically (bulk milk prices are determined in part by milk fat content).

It has now been discovered that the elfamycin and virginiamycin families of antibiotics are effective in improving milk production in lactating ruminants without causing an adverse affect upon milk quality. Such improvement has been mainifested in the form of increased milk volume without a decrease in fat content. The fact that this improvement can be realized is particularly surprising in view of the report by Parkhurst and McGowan in the 1978 Ellinbank Dairy Research Institute Report from Australia. These authors administered varying doses of monensin to dairy cows. Monensin is a polyether antibiotic widely employed as an enhancer of ruminant feed utilization efficiency. The authors concluded that, at all administration rates evaluated, fat-corrected-milk production was no different from that of non-treated control animals.

SUMMARY OF THE INVENTION

This invention concerns a method for improving lactation of lactating ruminants. More particularly, the invention provides a method for improving milk production in lactating ruminants having a developed rumen function. The method comprises orally administering to a lactating ruminant an effective amount of a compound selected from the virginiamycin or elfamycin families of antibiotics.

DETAILED DESCRIPTION

All of the compounds employed in the method of this invention are known in the prior art. Many are commercially available and are employed in the treatment of bacterial infections in animals as well as in the stimulation of growth in domestic animals such as poultry, swine, sheep and beef cattle.

The compounds employed in the lactation improvement method of this invention belong to the classes of antibiotics known as the virginiamycin family and the elfamycin family. The virginiamycins are characterized by comprising a macrocyclic lactone peptolide chemical structure. All of the members of the class can be assigned to either one of two basic structures referred to as A and B. The A group of antibiotics are polyunsaturated cyclic peptolides having a molecular weight of about 500. The B group are cyclic hexadepsipeptides of molecular weight of about 800. The entire virginiamycin family of antibiotics is extensively reviewed by Cocito in *Microbiol. Rev.*, 43, pp 145–198 (1979). The review article is incorporated herein by reference in order to illustrate the members of the virginiamycin family which can be employed in the method of this invention.

Representative members of the virginiamycin family which can be employed according to the method of this invention include doricin, patricin, vernamycin, etamycin, geminimycin, synergistin, mikamycin, ostreogrycin, plauracin (A2315), streptogramin, pristinamycin, pyostacin, virginiamycin, viridogrisein and griseoviridin.

Like other products of fermentation origin, many of the antibiotics of the virginiamycin family comprise more than one factor. For example, virginiamycin is comprised of components referred to as virginiamycins M1 and M2 as well as virginiamycins S1, S2, S3 and S4. Similarly, the virginiamycin-type antibiotic known as "A-2315" is comprised of at least three factors, A, B and C (see U.S. Pat. No. 3,923,980). Vernamycin is likewise comprised of factors A, B and C. The various factors of each of the virginiamycin-type antibiotics ar all usable in the method of this invention. Accordingly, when reference is made herein to a particular antibiotic, it is to be understood that included within that term are all of the various factors which can be employed individually or in combination with one another, or as a complex of all such factors. All that is necessary to practice the method of this invention is that an effective amount of a virginiamycin-type antibiotic or an elfamycin-type antibiotic be delivered in vivo to a ruminant having a developed rumen function and capable of producing milk.

Preferred antibiotics of the virginiamycin family which can be employed in the present method include A-2315 (referred to in Cocito as plauracin or madumycin), virginiamycin, griseoviridin, vernamycin, etamycin, mikamycin, ostreogrycin, viridogrisein, streptogramin and pristinamycin.

A particularly preferred method for improving ruminant lactation comprises administering a propionate increasing amount of A-2315 to a lactating ruminant.

The elfamycin family of compounds are antibiotics derived by fermentation of strains of streptomyces. Illustrative of the elfamycins which can be employed in the lactation improvement method of this invention are X-5108, mocimycin, efrotomycin, A21A, azdimycin and A40A.

The elfamycin known as X-5108 is also referred to as aurodox and goldinodox. This antibiotic is described in detail by Berger in U.S. Pat. No. Re. 28,700. Several esters of X-5108 which are said to promote growth in cattle are disclosed by Maehr in U.S. Pat. No. 4,218,560.

Mocimycin is an elfamycin also referred to as debromycin, kirromycin and Delvomycin. This compound is described in detail in U.S. Pat. No. 3,927,211.

Efrotomycin is described in U.S. Pat. No. 4,065,356. It is additionally known as FR-02A.

The elfamycin A21A is also called heneicomycin and is disclosed in U.S. Pat. No. 4,175,007. Similarly, A40A is additionally referred to as kirrothricin and is described in detail in Mahner in "Antibiotics and other Secondary Metabolites," Academic Press, 1978.

Azdimycin is a elfomycin antibiotic described by Nimeck et al. in U.S. Pat. No. 3,898,327.

As used throughout this specification and in the claims, the term "improved lactation" refers to any observed advantageous influence on ruminant milk production caused by the administration of a virginiamycin or elfamycin antibiotic. Typical lactation improvements include actual increases in milk volume production without substantial adverse affects on milk composition, i.e. fat and protein content. In dairy research, a common method of expressing milk production is the term "4% fat-corrected-milk" (FMC). This term equalizes milk production with differing fat percent on an energy basis. Accordingly, one manifestation of improved lactation provided by this invention is increased fat-corrected-milk production. Another typical lactation improvement is enhanced butterfat or protein content in the milk that is produced. Dairymen are paid premiums for increased amounts of butterfat in milk, therefore such lactation improvement renders milk production more profitable. Similarly, increasing milk's protein content is a valuable lactation improvement since only a small increase would significantly increase the amount of cheese that could be produced from the milk. These and similar lactation improvements are contemplated by this invention.

The method of improving lactation in ruminants such as dairy cows and goats provided by this invention is practiced in a manner similar to the methods for improving ruminant feed utilization and promoting ruminant growth employing antibiotics of the virginiamycin and elfamycin families. Cocito teaches, for example, that young feeder calves receiving about 20 to about 40 grams of a virginiamycin per ton of feed consumed exhibit an increase in the rate of weight gain of about 8 to about 12 percent. Calves receiving 80 grams per ton demonstrated over 13 percent increase in weight compared to non-treated animals.

In order to effect improvement in lactation according to this invention, an effective amount of a virginiamycin or elfamycin antibiotic will be orally administered to a lactating ruminant. "An effective amount" as used herein means an amount which, when delivered in vivo to a lactating ruminant animal, causes an observable improvement in milk production, for example an increase in the volume of milk produced by about 2 to about 15 percent relative to untreated animals. Such an effective amount which is to be administered will of course depend upon a number of factors, including the form in which the antibiotic is administered, the age and size of the lactating ruminant being treated, the particular virginiamycin or elfamycin employed, and similar factors commonly encountered by those skilled in the art of animal husbandry. The amount of a virginiamycin which is effective generally will be from about 0.1 to about 400 mg/kg of animal body weight per day, and more preferably from about 1.0 to about 100 mg/kg of animal body weight per day. The elfamycins will be administered at similar doses. A preferred embodiment of the invention comprises orally administering from about 1.0 to about 10.0 mg/kg/day of A-2315 to lactating ruminants such as dairy cows.

The antibiotics employed in the present method can be administered to lactating ruminants by any of several alternative methods. They can be formulated for suitable oral administration via the normal daily feed ration, as water additives, as lick blocks, or if desired the compounds can be formulated with slow release excipients such as polymers, waxes and the like, and administered in the form of a slow release ruminant pellet, capsule, implant or similar prolonged payout device which is capable of delivering the antibiotic to the rumen. Also, since the compounds to be employed in the present method are antibiotics of fermentation origin, they lend themselves to convenient stabilization for use in animal feeds by the marumerization process described in U.S. Pat. No. 4,048,268.

The method of the invention is preferably practiced by orally administering an antibiotic, especially an antibiotic of the virginiamycin family, to a lactating ruminant via the normal feed ration. For example, the antibiotic A-2315 can be added to ruminant feed at the rate of about 10 to about 30 grams per ton of feed. The antibiotics employed in this method generally will be administered as feed additives at the rate of about 5 to about 100 grams of active ingredient per ton of feed. The compounds can be formulated as feed pre-mixes for convenient addition to the normal animal feed ration. Such pre-mix formulations will contain about 1 to about 95 percent by weight of active ingredient admixed with conventional carriers by excipients such as soybean meal, rice hulls, starch, corn meal and the like.

As previously noted, a preferred method for improving milk production in lactating ruminants comprises the oral administration of the virginiamycin type antibiotic A-2315. Factor A of this antibiotic has been shown to be effective in altering the fermentation process in a developed rumen in both in vitro and in vivo tests. The following in vitro test was employed to demonstrate the ability of A-2315 factor A to increase rumen propionate and butyrate production.

Rumen fluid is obtained from a steer with a surgically-installed fistula opening into the rumen. The steer is maintained on a high-grain ration, the composition of which follows:

| | |
|---|---|
| 69.95% | coarse ground corn |
| 10.00% | ground corncobs |
| 8.00% | soybean meal (50% protein) |
| 5.00 | alfalfa meal |
| 5.00% | molasses |
| 0.60% | urea |
| 0.50% | dicalcium phosphate |
| 0.50% | calcium carbonate |
| 0.30% | salt |
| 0.07% | vitamins A and $D_2$ premix* |
| 0.05% | vitamin E premix** |
| 0.03% | trace mineral premix*** |

*Containing per pound:2,000,000 I.U. of vitamin A; 227,200 I.U. of vitamin $D_2$ and 385.7 g. of soybean feed with 1% oil added
**Corn distillers dried grains with solubles containing 20,000 I.U. of d-α-tocopheryl acetate per pound
***Containing manganous oxide, potassium iodide, cobalt carbonate, copper oxide and zinc sulfate A sample of rumen fluid is strained through four layers of cheesecloth, and the filtrate is collected. The particulate matter retained by the cheesecloth is resuspended in enough physiological buffer to return it to the original volume of the rumen fluid, and this suspension is strained again. The buffer used has the following composition:

| g/liter | Ingredient |
|---|---|
| 0.316 | $NH_2HPO_4$ |
| 0.152 | $KH_2PO_4$ |
| 2.260 | $NaHCO_3$ |
| 0.375 | KCl |
| 0.375 | NaCl |
| 0.112 | $MgSO_4$ |
| 0.050 | $CaCl_2 2H_2O$ |
| 0.008 | $FeSO_4 . 7H_2O$ |
| 0.004 | $MnSO_4 . H_2O$ |
| 0.004 | $ZnSO_4 . 7H_2O$ |
| 0.002 | $CuSO_4 . 5H_2O$ |
| 0.001 | $CoCl_2 . 6H_2O$ | as described by Chang et al. in J. Dairy Sci. 38, 1225–1230, (1955).

The two filtrates are combined and allowed to stand until particulate matter separates to the top. The clear layer is separated, diluted with the same buffer (1:1) and then adjusted to pH 7.0.

The diluted rumen fluid (10 ml.) is placed in a 25-ml flask with 40 mg. of the above-described feed, an additional 5 mg. of soybean protein, and the test compound. Four replicate flasks are used per treatment. Two sets of four control flasks each are also employed. A zero-time control and an incubated 16-hour control are used. All test flasks are incubated for 16 hours at 38° C. After incubation, 25 percent metaphosphoric acid (2 ml.) is added to each flask. The samples are allowed to settle, and the supernatant is analyzed by gas chromatography for propionate, acetate, and butyrate compounds.

Test compound results are statistically compared with control results. The table below shows the ratio of volatile-fatty-acid (VFA) concentrations in treated flasks to concentrations in control flasks.

TABLE I

| Activity of A-2315 Factor A on Ruminal VFA In Vitro | | | | |
|---|---|---|---|---|
| mcg A-2315-A per ml diluted rumen fluid | Acetate | Butyrate | Propionate | Total VFA |
| 1.0 | 0.95 | 1.04 | 1.15 | 1.05 |
| 0.3 | 0.95 | 1.00 | 1.08 | 1.07 |
| 0.1 | 0.97 | 1.01 | 1.07 | 1.04 |
| 0.0 | 1.00 | 1.00 | 1.00 | 1.00 |

An in vivo test designed to demonstrate the ability of A-2315A to increase propionate and butyrate in a developed rumen was carried out in non-lactating sheep.

Two groups of fistulated lambs are allowed slightly more than their normal feed ration for 17 days. Test compound is administered to one group in the feed on a g/ton basis.

The rumen fluids of both groups of animals are sampled on days 3, 7, 10, 14 and 17 of the treatment period.

The fermentation of the ruminal samples is halted by addition of meta-phosphoric acid. Each sample is diluted, centrifuged at 2000×gravity for 10 minutes; the supernatants are analyzed for volatile fatty acids via the gas chromatographic method of E. S. Erwin, G. J. Marco and E. M. Emery in J. Dairy Sci., 44, 1768 (1966). Molar percentages of ruminal volatile fatty acids are calculated, and the effect is measured as a comparison of the molar percentages of propionic acid and butyric acid in treated animals to those in contemporary controls. The results of the test are presented below in Tables II and III.

TABLE II

Activity of A-2315 Factor A on Ruminal VFA In Vivo

| Treatment | Amount | Number of Animals | % Propionic Acid Conc. | Change from Control | Increase Relative to Control |
|---|---|---|---|---|---|
| A-2315 Factor A | 15 g/ton | 6 | 31.0 | 4.8 | 18.2% |
| Control | | 6 | 26.2 | 0 | 0 |

TABLE III

Activity of A-2315 Factor A on Ruminal VFA In Vivo

| Treatment | Amount | Number of Animals | % Butyric Acid Conc. | Change from Control | Increase Relative to Control |
|---|---|---|---|---|---|
| A-2315 Factor A | 15 g/ton | 6 | 13.5 | 2.4 | 21.6% |
| Control | | 6 | 11.1 | | |

The practice of this invention will be further appreciated from the following detailed examples.

EXAMPLE 1

The following composition is a typical feedstuff to be administered to lactating ruminants in the practice of this invention.

| Ingredient | Percent by Weight |
|---|---|
| Corn | 32.15 |
| Barley | 10.0 |
| Molasses | 7.5 |
| Oats | 10.0 |
| Soybean Oil meal (48% protein) | 13.8 |
| Beet pulp | 2.5 |
| Corn Gluten feed | 12.5 |
| Distillers Grain | 7.5 |
| Trace Mineral Mix | 0.05 |
| Salt | 1.0 |
| Dicalcium Phosphate | 2.0 |
| | 100.00 |

The above ingredients are blended to uniformity and then an elfamycin or a virginiamycin antibiotic such as A-2315 is added at the rate of 30 grams per ton of feedstuff. The mixture is mixed thoroughly and fed to lactating ruminants such as dairy cows ad libitum for an increase in milk volume of about 4 to about 10 percent, without a concomitant decrease in milk butter fat content.

EXAMPLE 2

Another typical high protein diet for lactating ruminants is the following composition.

| Ingredient | Percent by Weight |
|---|---|
| Ground corn cob | 35.0 |
| Dehydrated alfalfa meal | 20.0 |
| Ground corn | 19.3 |
| Cane molasses | 12.0 |
| Soybean oil meal (48% protein) | 12.0 |
| Dicalcium phosphate | 1.0 |
| Iodized salt | 0.5 |
| Trace mineral mix | 0.17 |
| Vitamin A and D3 premix | 0.02 |
| Corn oil | 0.01 |
| | 100.00 |

The ingredients are blended to uniformity and then a virginiamycin antibiotic premix comprised of 30 grams of A-2315A admixed with one pound of ground corn cob is blended with the feed ration such that the final formulation contain about 30 grams of A-2315A per ton of feedstuff. The feedstuff is then administered to dairy animals ad libitum for an increase in milk production of about 4 to about 10 percent.

The ability of the virginiamycins to improve lactation in lactating ruminants has been demonstrated in an in vivo test employing thirty Holstein heifers. The animals were about 2½ years old, weighed approximately 1200 pounds at the time the test was started, and in general were about 18 weeks into lactation. The test followed a 2×3 factorial design, and consisted of a 10-week treatment period following a preliminary 2-week adjustment period. Each animal served as an experimental unit.

The animals were divided into two main groups of fifteen each. All of the animals in one group were fed a diet comprised of 50% (dry matter weight basis) corn silage and 50% protein concentrate having 19.9% protein and comprised of the following ingredients.

| Ingredients | weight % |
|---|---|
| Corn, ground yellow | 63.2 |
| Soybean meal | 21.9 |
| Brewer's Dried Grains | 10.0 |
| Limestone | 2.5 |
| Monosodium phosphate | .9 |
| Vit AD premix[a] | .35 |
| Vit E premix[b] | .10 |
| Se premix[c] | .05 |
| Trace mineral salt[d] | 1.0 |

[a]Each pound of premix contains $2 \times 10^6$ USP units vitamin A and $2.25 \times 10^5$ USP units of vitamin $D_3$.
[b]Each pound of premix contains $2 \times 10^4$ I.U. vitamin E.
[c]Each pound of premix contains 91 mg selenium.
[d]Trace mineralized salt contains between 95% and 98% salt, 0.28% manganese as manganous oxide, 0.007% iodine as calcium periodate, 0.007% cobalt as cobalt carbonate 0.035% copper as copper oxide, 0.35% zinc as zinc oxide, 0.175% iron as iron oxide.

The other group of fifteen test animals received a diet of 75% (dry matter weight basis) corn silage and 25% of a concentrate having 33.5% protein and having the following composition:

| Ingredients | weight % |
|---|---|
| Corn, ground yellow | 15.85 |
| Soybean meal | 50.15 |
| Brewer's Dried Grains | 20.0 |
| Molasses | 5.0 |
| Limestone | 4.15 |
| Monosodium phosphate | 1.85 |
| Vit AD premix[a] | .70 |
| Vit E premix[b] | .20 |
| Se premix[c] | .10 |
| Trace mineral salt[d] | 2.0 |

[a]Each pound of premix contains $2 \times 10^6$ USP units vitamin A and $2.25 \times 10^5$ USP units of vitamin $D_3$.
[b]Each pound of premix contains $2 \times 10^4$ I.U. vitamin E.
[c]Each pound of premix contains 91 mg selenium.
[d]Trace mineralized salt contains between 95% and 98% salt, 0.28% manganese as manganous oxide, 0.007% iodine as calcium periodate, 0.007% cobalt as cobalt carbonate 0.035% copper as copper oxide, 0.35% zinc as zinc oxide, 0.175% iron as iron oxide.

Within each of the two groups of fifteen animals, five were used as controls and received no antibiotic. Five of the animals in each group received a daily dose of 400 mg/head of the virginiamycin A2315, and the remaining five animals received 800 mg/head/day of A2315. In all cases, the A2315 was administered orally by mixing with two pounds of top dress for the daily feed ration.

Milk production and feed intake were recorded daily. Milk composition was determined weekly throughout the study. Rumen samples were collected every two weeks and analyzed for VFA composition. The results of the study are presented in the following tables.

TABLE IV

Milk Production (Pounds per day)

| | Dosage of A2315 (mg/head/day) | | |
|---|---|---|---|
| | 0 | 400 | 800 |
| Lactating ruminants on diet of: | | | |
| 50% corn silage > 50% concentrate | 40.8 | 44.7 | 43.4 |
| % change from non-treated control | | 9.6 | 6.4 |
| Lactating ruminants on diet of: | | | |
| 75% corn silage > 25% concentrate | 40.5 | 40.0 | 40.9 |
| % change from non-treated control | | −1.3 | 1.0 |

TABLE V

Milk Composition (% milk fat)

| | Dosage of A2315 (mg/head/day) | | |
|---|---|---|---|
| | 0 | 400 | 800 |
| Lactating ruminants on diet of: | | | |
| 50% corn silage > 50% concentrate | 3.25 | 3.30 | 3.27 |
| 75% corn silage > 25% concentrate | 3.66 | 3.69 | 3.54 |

TABLE VI

Milk Composition (% protein)

| | Dose of A2315 (mg/head/day) | | |
|---|---|---|---|
| Ration | 0 | 400 | 800 |
| 50:50 | 3.53 | 3.45 | 3.46 |
| 75:25 | 3.48 | 3.48 | 3.45 |

TABLE VII

Rumen VFA concentrations for animals on 50:50 corn silage/concentrate diet

| | Volatile Fatty Acids | | | |
|---|---|---|---|---|
| Dose of A2315 mg/head/day | Acetate | (molar %) Propionate | Butyrate | Total VFAs mmoles/l |
| 0 | 62.4 | 23.9 | 13.0 | 60.1 |
| 400 | 60.9 | 22.9 | 16.1 | 54.9 |
| 800 | 61.3 | 23.5 | 15.3 | 58.3 |

TABLE VIII

Rumen VFA concentrations for animals on 75:25 corn silage/concentrate diet

| | Volatile Fatty Acids | | | |
|---|---|---|---|---|
| Dose of A2315 mg/head/day | Acetate | (molar %) Propionate | Butyrate | Total VFAs mmoles/l |
| 0 | 65.8 | 22.0 | 12.3 | 60.4 |
| 400 | 64.8 | 20.4 | 14.8 | 55.4 |
| 800 | 65.6 | 19.1 | 15.3 | 52.2 |

I claim:

1. A method for improving lactation in lactating ruminants comprising orally administering to a lactating ruminant having a developed rumen function an effective amount of an antibiotic which is a member of the virginiamycin family of antibiotics or the elfamycin family of antibiotics.

2. The method of claim 1 employing a virginiamycin antibiotic selected from doricin, patricin, vernomycin, etamycin, geminimycin, synergistin, mikamycin, ostreogrycin, plaurocin (A-2315), streptogramin, pristinamycin, pyostacin, virginiamycin, viridogrisein, or griseoviridin.

3. The method of claim 2 wherein the antibiotic employed is selected from the A-2315 antibiotic complex or the individual factors thereof.

4. The method of claim 3 wherein the antibiotic employed is A-2315 complex.

5. The method of claim 3 wherein the antibiotic employed is A-2315A.

6. The method of claim 2 wherein the antibiotic employed as virginiamycin M1 or virginiamycin M2.

7. The method of claim 1 employing an elfamycin antibiotic selected from mocimycin, aurodox (X-5108), efrotomycin, A21A, A40A or azdimycin.

8. The method of claim 7 employing X-5108.

* * * * *